United States Patent
Gorgojo Lobato et al.

(10) Patent No.: US 7,057,045 B2
(45) Date of Patent: Jun. 6, 2006

(54) PROCESS FOR OBTAINING 17β-(SUBSTITUTED)-3-OXO-Δ$^{1,2}$-4-AZASTEROIDS AND INTERMEDIATES

(75) Inventors: Jose Maria Gorgojo Lobato, Boecillo (ES); Antonio Lorente Bonde-Larsen, Boecillo (ES); Jorge Martin Juarez, Boecillo (ES)

(73) Assignee: Ragactives, S.L., Valladolid (ES)

( * ) Notice: Subject to any disclaimer, the term of this patent is extended or adjusted under 35 U.S.C. 154(b) by 0 days.

(21) Appl. No.: 10/810,128

(22) Filed: Mar. 26, 2004

(65) Prior Publication Data
US 2004/0254209 A1 Dec. 16, 2004

Related U.S. Application Data

(63) Continuation of application No. PCT/ES02/00453, filed on Sep. 26, 2002.

(51) Int. Cl.
*C07D 221/18* (2006.01)
*C07D 498/06* (2006.01)
(52) U.S. Cl. .......................... 546/77; 546/47

(58) Field of Classification Search ................. 546/47, 546/77
See application file for complete search history.

(56) References Cited

U.S. PATENT DOCUMENTS 5,021,575 A * 6/1991 King et al. ................ 546/77

* cited by examiner

*Primary Examiner*—Charanjit S. Aulakh
(74) *Attorney, Agent, or Firm*—Akin Gump Strauss Hauer & Feld, LLP

(57) ABSTRACT

The 17β-(substituted)-3-oxo-Δ$^{1,2}$-4-azasteroids (I), wherein $R^1$ is $C_1$–$C_4$ alkyl, $OR^2$, wherein $R^2$ is a $C_1$–$C_4$ alkyl radical, or $NR^3R^4$, wherein $R^3$ and $R^4$, equal or different, represent hydrogen or a $C_1$–$C_4$ alkyl radical, can be obtained by means of a process comprising cleaving the oxazolidinedione ring present in a 2-(substituted)-3-hydroxyoxazolidinedione of formula (IV), wherein $R^5$ is Br or trichloromethylsulfonyl, and removing the substituent at position 2, to form a double bond at position 1,2. Some compounds (I) are testosterone-5α-reductase inhibitors and can be used in the treatment of hyperandrogenic disorders.

15 Claims, No Drawings

PROCESS FOR OBTAINING 17β-(SUBSTITUTED)-3-OXO-Δ$^{1,2}$-4-AZASTEROIDS AND INTERMEDIATES

CROSS-REFERENCE TO RELATED APPLICATIONS

This application is a continuation of International Application No. PCT/ES02/00453, filed Sep. 26, 2002, the disclosure of which is incorporated herein by reference.

BACKGROUND OF THE INVENTION

The invention refers to a process for producing 17β-(substituted)-3-oxo-Δ$^{1,2}$-4-azasteroids by dehydrogenation of 4-azasteroids at position 1,2, as well as to intermediates formed and/or used in said process. Some of said compounds are testosterone-5α-reductase inhibitors and can be used in the treatment of hyperandrogenic disorders.

The synthesis of 17β-(substituted)-3-oxo-Δ$^{1,2}$-4-azasteroids can be carried out by means of the dehydrogenation of azasteroids, particularly 17β-(substituted)-3-oxo-4-azasteroids, in order to obtain the corresponding compound with a double bond at position 1,2.

The state of the art discloses several processes for dehydrogenating 4-azasteroids and, particularly, 3-oxo-4-azasteroids substituted at position 17β. Spanish patent ES 8,702,430 discloses a process for introducing a double bond at position 1,2 of 4-azasteroids by treatment with benzeneseleninic anhydride in refluxing chlorobenzene. European patent EP 298,652 discloses a dehydrogenation process comprising the oxidation of a silyl enol ether derivative with a DDQ-type quinone [4,5-dichloro-3,6-dioxo-1,4-cyclohexadiene-1,2-dicarbonitrile]. European patents EP 473,225 and 473,226 disclose processes comprising the formation of silyl enol ethers with halides or trialkylsilyl triflates, subsequent addition of halogen to the double bond at position 2,3 and dehydrohalogenation.

European patent EP 428,366 discloses the process shown in the following diagram:

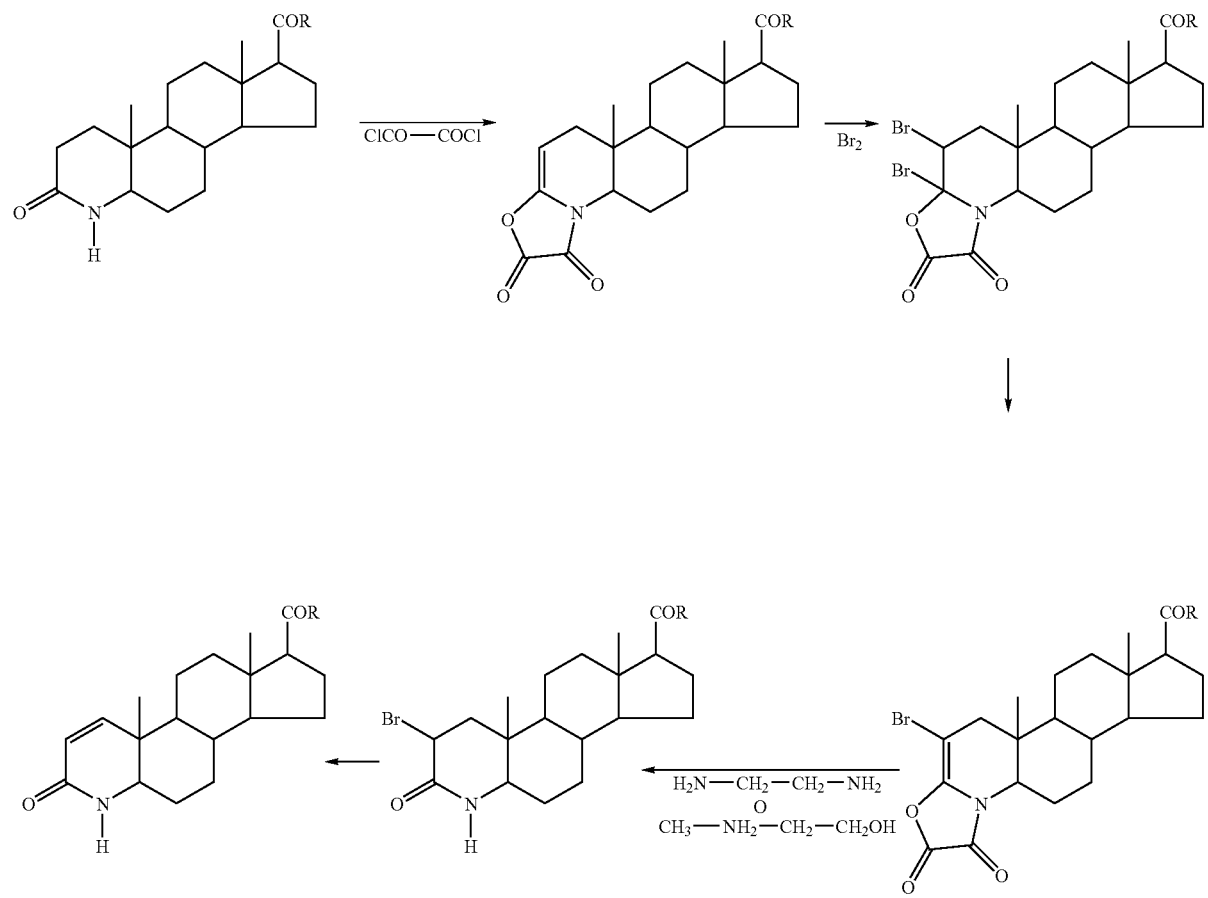

As can be seen, a 17β-(substituted)-3-oxo-4-azasteroid reacts with an oxalyl chloride to form the corresponding adduct which, by means of reaction with bromine, provides the compound 2,3-dibromate. The dibromate intermediate is decomposed into the 2-bromine derivative providing 17β-(substituted)-2-bromo-3-oxo-4-azasteroid by means of reaction with ethylenediamine or 2-methylaminoethanol by means of a transamidation and/or transesterification reaction. The dehydrobromation carried out with conventional reagents gives rise to the dehydrogenation product.

Said European patent EP 428,366 mentions that all intermediates leading to 2-bromo-5α-azasteroid-type products are water sensitive, this one should therefore be strictly excluded from the reaction. According to said European patent, the products of degradation with water of said intermediates are those shown in the following diagram:

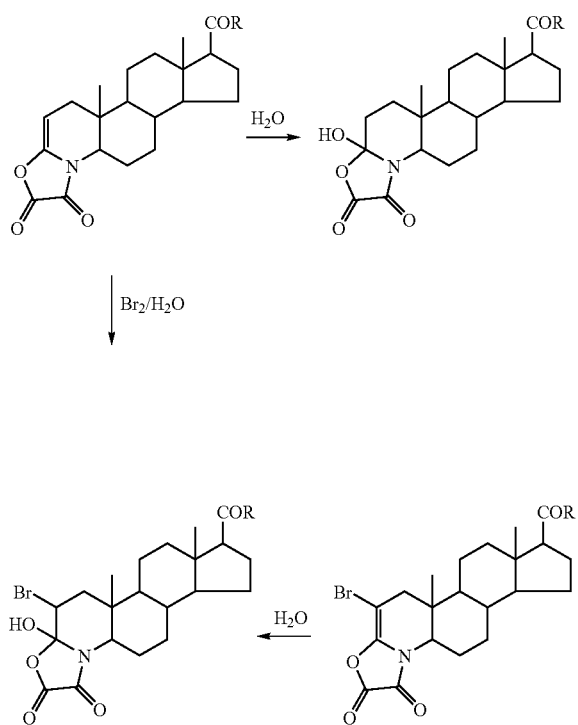

Even though such degradation products, both the 3-hydroxy derivative and the 2-bromo-3-hydroxy derivative, are represented in the diagram shown in European patent EP 428,366, said patent discloses neither its obtainment nor its characterization. Likewise, the only example (Example 1) contained in said EP 428,366 discloses a process in which none of the synthesis intermediates are isolated, nor does it provide physical constants or structural identification spectroscopic data.

The majority of processes known for the dehydrogenation of 17β-(substituted)-3-oxo-4-azasteroids comprise the use of toxic selene reagents or reagents which are hazardous to handle (bromine), or expensive, such as trimethylsilyl triflate, therefore there is a need to develop alternative processes which overcome such drawbacks.

The invention proposes a new method for obtaining 17β-(substituted)-3-oxo-$\Delta^{1,2}$-4-azasteroids of formula (I) from 2-(substituted)-3-hydroxyoxazolidinedione of formula (IV).

The solution provided by this invention is based on the fact that the inventors have surprisingly seen that it is possible to carry out the cleavage of the oxazolidinedione ring present in a 2-(substituted)-3-hydroxyoxazolidinedione of formula (IV), using the reaction conditions provided in the invention, to produce a 2-(substituted)-3-oxo-4-azasteroid of formula (V) which, by removal of the substituent group at position 2, provides a 17β-(substituted)-3-oxo-$\Delta^{1,2}$-4-azasteroid of general formula (I) with good yields.

A process like the one provided by this invention has the advantage of not using toxic or hazardous reagents, and furthermore, the intermediates used and/or formed in said process are stable enough in contact with water that they can be easily isolated, purified and stored.

BRIEF SUMMARY OF THE INVENTION

Therefore, an object of this invention is constituted by a process for producing a 17β-(substituted)-3-oxo-$\Delta^{1,2}$-4-azasteroid of formula (I) comprising the cleavage of the oxazolidinedione ring present in a 2—(substituted)-3-hydroxyoxazolidinedione of formula (IV) and the removal of the substituent at position 2.

A further object of this invention is constituted by said 2—(substituted)-3-hydroxyoxazolidinedione of formula (IV). The use of said compound in the production of 17β-(substituted)-3-oxo-$\Delta^{1,2}$-4-azasteroids constitutes a further object of this invention.

Another further object of this invention is constituted by a process for obtaining said 2-(substituted)-3-hydroxyoxazolidinediones of formula (IV) from vinylidenyloxazolidinediones of formula (III).

Another further object of this invention is constituted by a process for the synthesis of said 2-(substituted)-3-hydroxyoxazolidinedione of formula (IV) by reaction of a 4-azasteroid with oxalyl chloride to produce vinylidenyloxazolidinedione of formula (III), which is reacted with a compound chosen from between a reagent capable of adding hypobromous acid to a double bond and a trichloromethylsulfonyl halide for the purpose of introducing a substituent (bromine or trichloromethylsulfonyl) at position 2 of the 4-azasteroid and forming said 2-(substituted)-3-hydroxyoxazolidinedione of formula (IV).

Another further object of this invention is constituted by a process for producing 17β-(substituted)-3-oxo-$\Delta^{1,2}$-4-azasteroids of formula (I) by dehydrogenation of 4-azasteroids at position 1,2, comprising a) reacting a 4-azasteroid with oxalyl chloride to produce a vinylidenyloxazolidinedione of formula (III); b) reacting said vinylidenyloxazolidinedione of formula (III) with a compound chosen from between a reagent capable of adding hypobromous acid to a double bond and a trichloromethylsulfonly halide to produce a 2-(substituted)-3-hydroxyoxazolidinedione of formula (IV); c) cleaving the oxazolidinedione ring present in said 2-(substituted)-3-hydroxyoxazolidinedione of formula (IV); and d) removing the substituent present at position 2 of said 2-(substituted)-3-hydroxyoxazolidinedione of formula (IV).

DETAILED DESCRIPTION OF THE INVENTION

The invention provides a process for producing a 17β-(substituted)-3-oxo-$\Delta^{1,2}$-4-azasteroid of formula (I)

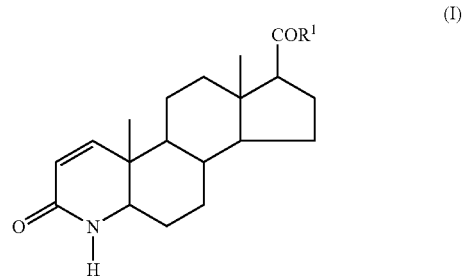

wherein $R^1$ is a linear or branched alkyl group having 1 to 4 carbon atoms; $OR^2$, wherein $R^2$ is a linear or branched alkyl radical having 1 to 4 carbon atoms; or $NR^3R^4$, wherein $R^3$ and $R^4$, equal or different, represent hydrogen or a linear or branched alkyl radical having 1 to 4 carbon atoms, comprising the steps of:

a) cleaving the oxazolidinedione ring present in a 2-(substituted)-3-hydroxyoxazolidinedione of formula (IV):

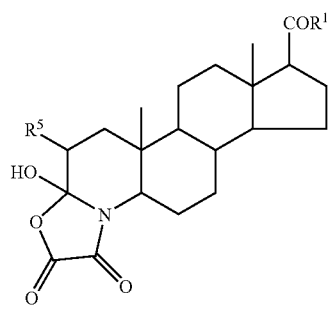

(IV)

wherein $R^1$ has the previously mentioned significance and $R^5$ is chosen from between Br and trichloromethylsulfonyl; to produce a 2-(substituted)-3-oxo-4-azasteroid of formula (V):

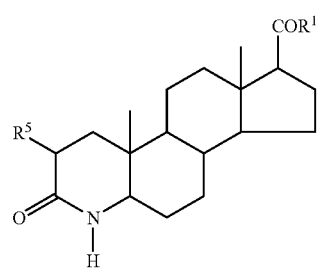

(V)

wherein $R^1$ and $R^5$ have the previously mentioned significance; and b) removing the $R^5$ substituent present in said compound of formula (V), together with a hydrogen at position 1, to produce said 17β-(substituted)-3-oxo-$\Delta^{1,2}$-4-azasteroid of formula (I).

The compounds of formula (I) can have different stereoisomers, all of which fall within the scope of the present invention and can be obtained by means of the process provided by this invention. Some compounds of formula (I) obtained by means of the previously disclosed process are testosterone-5α-reductase inhibitors, thereby being useful for the treatment of hyperandrogenic disorders. In this sense, a particularly preferred compound of formula (I) is finasteride [17β-(N-t-butylcarbamoyl)-4-aza-5-α-androst-1-ene-3-one], used in the treatment of benign prostate hyperplasia and of hyperandrogenic alopecia. Other compounds of formula (I) can be used as intermediates for the synthesis of finasteride.

Cleavage of the oxazolidinedione ring present in said compound of formula (IV) to produce a compound of formula (V) cannot be carried out by means of conventional methods for removing the carbon dioxide radical, like those mentioned in European patent EP 428,366, for example, by transamination or transesterification, using ethylenediamine, dialkylethylenediamine, 2-methylaminoethanol or ethylene glycol. This cleavage can surprisingly be carried out by means of a novel method not disclosed in the state of the art, in which said oxazolidinedione ring is cleaved by potassium permanganate oxidation with carbon dioxide loss by using an alcohol as a solvent such as methanol, a cetone, such as acetone, a halogenated solvent, such as methylene chloride or 1,2-dichloroethane, or mixtures of said solvents with water. The reaction can be carried out at a temperature comprised between 0° C. and 80° C., preferably at room temperature (15–25° C.), and the reaction time can range between 5 minutes and 24 hours, normally 5 minutes at room temperature. The reaction product [compound of formula (V)] is recovered as a mixture of 2α and 2β-(substituted)-17β-(substituted)-3-oxo-4-azasteroid isomers.

Removal of the $R^5$ substituent ($R^5$=Br or $CCl_3SO_2$) present in said compound of formula (V), together with a hydrogen at position 1, to produce a compound of formula (I), can be carried out by means of the use of potassium tert-butoxide in DMF (see for example EP 428,366) at a temperature comprised between −10° C. and 25° C.

The compounds of formula (IV) are new products, useful as intermediates in the synthesis of compounds of formula (I), and they constitute, together with the process for their obtainment, a further object of this invention.

The compounds of formula (IV) can have different stereoisomers, all of which fall within the scope of the present invention. Particularly preferred compounds of formula (IV) include those in which $R^1$ is t-butylamino or methoxy and $R^5$ is Br or trichloromethylsulfonyl, and the hydrogen atom configuration at position 5 of the azasteroid is α, useful as intermediates for the synthesis of finasteride.

The compounds of formula (IV) can be obtained by means of a process comprising reacting a compound of formula (III)

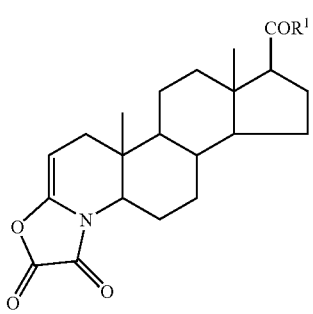

(III)

wherein $R^1$ is a linear or branched alkyl group having 1 to 4 carbon atoms; $OR^2$, wherein $R^2$ is a linear or branched alkyl radical having 1 to 4 carbon atoms; or $NR^3R^4$, wherein $R^3$ and $R^4$, equal or different, represent hydrogen or a linear or branched alkyl radical having 1 to 4 carbon atoms; with a compound chosen from between:

(i) a reagent capable of adding hypobromous acid to the double bond at position 2,3 of the compound of formula (II); and (ii) a trichloromethylsulfonyl halide, to produce a compound of formula (IV):

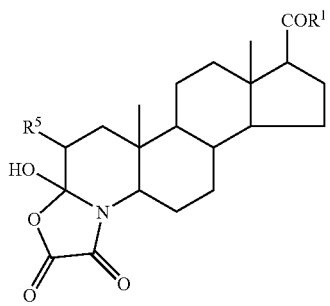

(IV)

wherein R¹ has the previously mentioned significance, and R⁵ is chosen from between Br and trichloromethylsulfonyl.

The reagent capable of adding hypobromous acid to the double bond at position 2,3 of the compound of formula (III) can be any reagent which, by reaction with the compound of formula (III), produces the corresponding bromhydrin. Illustrative examples of said reagents include N-bromosuccinimide or 1,3-dibromo-5,5-dimethylhydantoin. The reaction of the compound of formula (III) with said reagent capable of adding hypobromous acid to the double bond to produce the corresponding bromhydrin [compound of formula (IV) wherein R⁵ is Br] is carried out in an organic solvent, such as acetone, in presence of an inorganic acid, for example perchloric acid in aqueous solution, at a temperature comprised between −20° C. and 25° C. and for a time period comprised between 30 minutes and 2 hours. Once the reaction has finished, the reagent excess is neutralized with aqueous solution of a reducing agent, for example sodium metabisulfite, and the reaction product [compound of formula (IV), wherein R⁵ is bromine] is recovered by filtration.

The reaction of the compound of formula (III) with trichloromethylsulfonyl halide to produce a compound of formula (IV) wherein R⁵ is trichloromethylsulfonyl, is carried out in an organic solvent, such as halogenated solvent, for example methylene chloride or 1,2-dichloroethane, in presence of an organic base, such as diisopropylethylamine (DIPEA), at a temperature comprised between −10° C. and 80° C. Once the reaction has finished, an aqueous solution of an inorganic acid, such as hydrochloric acid, is added, the phases are separated, and the organic phase is treated so as to isolate the reaction product [compound of formula (IV), wherein R⁵ is trichloromethylsulfonyl].

The vinylidenyloxazolidinediones of formula (III) can be obtained by means of a process comprising reacting a 17β-(substituted)-3-oxo-4-azasteroid of formula (II):

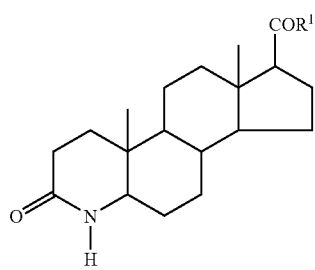

(II)

wherein R1 is a linear or branched alkyl group having 1 to 4 carbon atoms; OR², wherein R² is a linear or branched alkyl radical having 1 to 4 carbon atoms; or NR³R⁴, wherein R³ and R⁴ equal or different, represent hydrogen or a linear or branched alkyl radical having 1 to 4 carbon atoms; with oxalyl chloride to produce said vinylidenyloxazolidinedione of formula (III).

The transformation reaction of a compound of formula (II) into a compound of formula (III) can be carried out by conventional methods disclosed in the state of the art [see for example EP 428,366], or, preferably, by means of an alternative process to the one disclosed in the state of the art, by treatment with oxalyl chloride in an halogenated solvent, for example methylene chloride, chloroform or carbon tetrachloride, and by using a combination of 2 nitrogenous organic bases which are used in two phases of the reaction, such as pyridine (at −40° C.) and diisopropylethylamine (between −40° C. and −10° C.). Once the reaction is finished, the compound of formula (III) can be isolated by removing the basic remains by washing with an aqueous acid solution (such as hydrochloric acid), wherein the compound of formula (III) is stable and subsequent distillation of the solvent. The compound of formula (III) can be purified and isolated by means of a recrystallization or resuspension in general use solvents, such as heptane, acetonitrile or methanol. Alternately, if desired, the compound of formula (III) can be converted into the compound of formula (IV) according to the previously described method without needing to isolate it.

The compounds of formula (II) are either known and commercially available products, or they can be synthesized by means of methods disclosed in the state of the art [see for example U.S. Pat. No. 4,760,071].

The invention also provides a process for producing a 17β-(substituted)-3-oxo-Δ¹,²-4-azasteroid of formula (I) comprising reacting said compound of formula (II) with oxalyl chloride to produce said compound of formula (III), which is reacted with a compound chosen from between (i) a reagent capable of adding hypobromous acid to the double bond and (ii) a trichloromethylsulfonyl halide, to produce said compound of formula (IV), followed by cleavage of the oxazolidinedione ring present in the compound of formula (IV) to produce the compound of formula (V) and subsequent treatment of said compound of formula (V), under suitable conditions, to produce the compound of formula (I). The conditions for carrying out each one of the steps are those mentioned previously for each particular reaction. The intermediates of formula (III) and (IV), if so desired, can be isolated either by conventional methods or, if so desired, after the removal of all or part of the contaminants, can be used directly in the oxazolidinedione ring cleavage reaction.

It has been surprisingly found that the intermediate compounds of formulas (III) and (IV) are stable enough in contact with water, therefore these products can be isolated by means of liquid-liquid extractions, in which one of the phases is aqueous, and in addition the transformation reaction of a compound of formula (III) into a compound of formula (IV) can be carried out in a water-containing medium, without no significant degradation of the compounds in the reaction medium, nor during the isolation steps. In fact, the compounds of formula (III) and (IV) can be isolated as solid products, purified and characterized by conventional structural identification methods. Likewise, it has been found that the compounds of formula (IV) are useful intermediates for obtaining 2-bromo-4-azasteroids, unlike that disclosed in the state of the art [EP 428,366], in which such compounds are considered simple degradation products of the intermediates of the disclosed process.

The possibility of isolation of the intermediate of both (III) and (IV) helps the obtention of the starting materials with the desired purity such as, for example, for obtaining products of general formula (V) susceptible to being transformed into the corresponding products 17β-(substituted)-3-oxo-Δ$^{1,2}$-24-azasteroid of general formula (I).

The following examples serve to illustrate the present invention, and they should not be considered limiting thereof.

EXAMPLE 1

Compound of Formula (III), Wherein R$^1$ is t-butylamine 100 g of 17β-(N-t-butylcarbamoyl)-4-aza-5α-androstan-3-one and 36.6 ml of dry pyridine are dissolved under inert atmosphere in 1 L of dry methylene chloride. Then, it is cooled at −45° C., and 25.7 mL of oxalyl chloride are added, keeping the temperature below −35° C. The temperature is maintained at approximately −40° C. for 5 or 10 minutes, 78.7 mL of dry diisopropylethylamine are added, and the temperature is increased up to −10° C., maintaining it for about 45 minutes. Immediately after, the reaction mixture is poured over 1 L of 10% hydrogen chloride aqueous solution previously cooled at −10° C. The phases are separated, and the organic phase is washed with 1 L of water and evaporated to dryness, thereby obtaining a mass of 126 g of a yellow solid.

The obtained solid is resuspended in 250 mL of methanol previously cooled at 0° C. and stirred, maintaining the temperature for 30 minutes. It is filtered and washed with 100 mL of cold methanol and dried in a hot air circulation oven at 60° C. 91.65 g of the title purified vinylidenyloxazolidine-dione are thus obtained.

NMR-$^1$H (CDCl$_3$): 0.63 (s, 3H, CH$_3$), 0.79–0.99 (m, overlapped with s at 0.88), 0.88 (s, 3H, CH$_3$), 1.28 (s, 9H, $^t$Bu), 1.05–2.10 (m), 2.19 (dd, J=17.1, 6.7 Hz, 1H, H$_a$-1), 3.03 (m, 1H, H$_e$-1), 3.52 (dd, J=12.2, 3.6 Hz, 1H, H-5), 4.86–4.88 (m, 1H, H-2), 5.14 (s, 1H, H—N).

NMR-$^{13}$C (CDCl$_3$): 12.7 (CH$_3$), 12.9 (CH$_3$), 20.8 (CH$_2$), 22.6 (CH$_2$), 23.0 (CH$_2$), 24.0 (CH$_2$), 28.8 (CH$_3$, $^t$Bu), 29.2 (CH$_2$), 34.3 (CH), 34.3 (CH$_2$), 36.1 (C), 38.0 (CH$_2$), 43.4 (C), 50.8 (CH), 51.2 (C, $^t$Bu), 55.1 (CH), 57.1 (CH), 64.1 (CH), 85.8 (CH, C$_2$), 139.9 (C, C$_3$), 149.7 (C, carbonylic), 155.5 (C, carbonylic), 171.5 (C, C$_{20}$).

EXAMPLE 2

Compound of Formula (III), Wherein R$^1$ is Methoxy 11.95 g of 17β-(methoxycarbonyl)-4-aza-5α-androstan-3-one and 4.92 mL of dry pyridine are added under inert atmosphere in 120 mL of dry methylene chloride. The reaction mixture is cooled at −45° C., and 3.44 mL of oxalyl chloride are added dropwise, keeping the temperature below −35° C., and it is stirred, keeping the temperature below −40° C. for 10 minutes. 10.56 mL of diisopropylethylamine are added, the temperature of the mixture is increased up to −10° C. and is maintained for 45 minutes. 120 mL of 10% hydrogen chloride aqueous solution previously cooled at −10° C. are added, and it is stirred for 10 minutes. The phases are separated, the organic phase is washed with 120 mL of water and evaporated to dryness, obtaining 13.71 g of crude vinylidenyloxazolidinedione.

The obtained crude is resuspended in 24 mL of methanol previously cooled at −5° C., and is stirred, maintaining the temperature for 45 minutes. It is filtered and washed portionwise with 5 mL of cold methanol. It is dried in a hot air circulation oven (60° C.), obtaining 13.0 g of the title purified vinylidenyloxazolidinedione.

NMR-$^1$H (CDCl$_3$): 0.64 (s, 3H, CH$_3$), 0.85–1.20 (m, 3H) 0.91 (s, 3H, CH$_3$), 1.24–1.41 (m, 4H), 1.51–1.52 (m, 1H), 1.71–1.86 (m, 4H), 1.96–2.02 (m, 2H), 2.05–2.15 (m, 1H), 2.17–2.25 (m, 1H), 2.30–2.35 (m, 1H), 3.06–3.09 (m, 1H, H$_e$-1), 3.52–3.56 (m, 1H, H-5), 3.64 (s, 3H, OCH$_3$), 4.88–4.91 (m, 1H, H-2).

NMR-$^{13}$C (CDCl$_3$): 12.85 (CH$_3$), 13.44 (CH$_3$), 20.88 (CH$_2$), 22.77 (CH$_2$), 23.47 (CH$_2$), 24.23 (CH$_2$), 29.39 (CH$_2$), 34.51 (CH$_2$), 34.57 (CH), 36.30 (C), 37.90 (CH$_2$), 43.86 (C), 51.24 (CH), 51.36 (CH$_3$, OCH$_3$), 55.02 (CH), 55.02 (CH), 64.24 (CH), 85.79 (CH, C$_2$), 140.12 (C, C$_3$), 149.91 (C, carbonylic), 155.61 (C, carbonylic), 174.19 (C, ester carbonyl).

EXAMPLE 3

Compound of Formula (IV), Wherein R$^1$ is t-butylamine and R$^5$ is Bromine

A mixture of 1.82 L of acetone, 0.124 L of water and 3.66 mL of 70% aqueous perchloric acid is prepared under inert atmosphere. It is cooled to less than −20° C. and kept out of the light. 31.6 g of 1,3-dibromo-5,5-dimethylhydantoin are charged. 91 g of the vinylidenyloxazolidinedione obtained in Example 1 are charged, portionwise, over the course of 30 minutes, and it is stirred, maintaining the temperature for 10 additional minutes. When the reaction is finished (slight additional reagent excesses can be added to complete it), 10.8 g of potassium acetate and 3.23 g of sodium metabisulfite are charged. The reaction mixture is left to rise room temperature and it is distilled under vacuum conditions until reducing the volume to 640 mL. 700 mL of water are slowly added. The obtained white suspension is stirred for 30 minutes, filtered and washed with 91 mL of a 1.1/1 water/acetone mixture and finally dried, obtaining 114 g of the title 2-bromo-3-hydroyoxazolidinedione.

NMR-$^1$H (DMSO-d$_6$): 0.53 (s, 3H, CH$_3$), 0.78–1.10 (m, 3H), 0.92 (s, 3H, CH$_3$), 1.14–1.37 (m, 4H), 1.22 (s, 9H, $^t$Bu), 1.43–1.65 (m, 3H), 1.69–1.78 (m, 3H), 1.97–2.24 (m, 3H), 3.36 (dd, J=12.7, 2.9 Hz, 1H, H-5), 4.64 (dd, J=12.6, 4.2 Hz, 1H, H-2), 6.90 (s, 1H, N—H), 9.10 (s br, 1H, H-0).

NMR-$^{13}$C (DMSO-d6): 12.2 (CH$_3$), 13.6 (CH$_3$), 21.0 (CH$_2$), 23.1 (CH$_2$), 23.1 (CH$_2$), 24.4 (CH$_2$), 28.9 (CH$_3$, $^t$Bu), 30.3 (CH$_2$), 34.2 (CH), 37.4 (CH$_2$) 41.9 (C), 43.6 (C), 45.4 (CH$_2$), 50.1 (C, $^t$Bu), 50.1 (CH), 51.1 (CH), 55.0 (CH), 55.7 (CH), 62.0 (CH, C$_5$), 104.5 (C, C$_3$), 151.4 (C, carbonylic), 158.8 (C, carbonylic), 170.7 (C, C$_{20}$).

EXAMPLE 4

Compound of Formula (IV), Wherein R$^1$ is Methoxy and R$^5$ is Bromine

A mixture of 256 mL of acetone, 17.4 mL of water and 0.57 mL of 70% aqueous perchloric acid is prepared under inert atmosphere. The reaction mixture is cooled to less than −20° C. and kept out of the light. 4.91 g of 1,3-dibromo-5,5-dimethylhydantoin are charged. 12.79 g of the vinylidenyloxazolidinedione obtained in Example 1 are charged portionwise over the course of 30 minutes, and the reaction mixture is stirred, maintaining the temperature for an additional 10 minutes. When the reaction is finished (slight additional reagent excesses can be added to complete it), 1.69 g of potassium acetate and 0.50 g of sodium metabisulfite are charged. The reaction mixture is left to reach room temperature and the solvent is distilled under vacuum conditions until reducing the total volume to 90 mL. Then, 77 mL of water are slowly added, the obtained white suspension is stirred for 30 minutes, filtered and washed with 15 mL of a 1.1/1 water/acetone mixture and dried, obtaining 14.51 g of the title 2-bromo-3-hydroyoxazolidinedione.

NMR-$^1$H (DMSO-d6): 0.57 (s, 3H, $CH_3$), 0.88–0.95 (m, 2H), 0.93 (s, 3H, $CH_3$), 1.05–1.15 (m, 1H), 1.16–1.26 (m, 3H), 1.27–1.39 (m, 1H), 1.40–1.51 (m, 1H), 1.55–1.65 (m, 1H), 1.70–1.79 (m, 3H), 1.85–2.05 (m, 3H), 2.15–2.27 (m, 2H), 2.30–2.39 (m, 1H), 3.34 (m overlap with DMSO-$d_6$ signal, 1H, H-5), 3.57 (s, 3H, $OCH_3$), 4.66 (m, 1H, H-2), 8.96 (s, H—O).

NMR-$^{13}$C (DMSO-d6): 12.06 ($CH_3$), 13.39 ($CH_3$), 20.73 ($CH_2$), 22.88 ($CH_2$), 23.20 ($CH_2$), 23.93 ($CH_2$), 30.04 (CH), 34.05 ($CH_2$), 37.53 ($CH_2$), 41.76 (C), 43.62 (C), 45.30 ($CH_2$), 49.99 (CH), 50.65 (CH), 51.15 ($CH_3$, $OCH_3$), 54.30 (CH), 54.36 (CH), 61.82 (CH), 104.29 (C, $C_3$), 151.20 (C, carbonylic), 158.63 (C, carbonylic), 173.58 (C, $C_{20}$).

EXAMPLE 5

Compound of Formula (IV), Wherein $R^1$ is t-butylamine and $R^5$ is Trichloromehtylsulfonyl 8.54 g of the vinylidenyloxazolidinedione amide obtained in Example 1 and 14.5 mL of DIPEA are dissolved under nitrogen in 178 mL of dry methylene chloride. It is cooled to under −30° C.; 5.75 g net of trichloromethylsulfonyl are added, and the reaction mixture is left to rise room temperature. When the reaction is finished (4 hours at room temperature), the reaction mixture is poured over 200 mL of a 10% hydrogen chloride aqueous solution, the phases are separated and the organic phase is washed with 3 fractions of 100 mL of water and evaporated to dryness. The residue is dissolved with 45 mL of acetone and is distilled, reducing the volume to 18 mL. It is cooled at 0° C., filtered and dried, obtaining 7.24 g of the title 2-(trichloromethylsulfonyl)-3-hydroxyoxazolidinedione as a white solid.

NMR-$^1$H (DMSO-d6): 0.54 (s, 3H, $CH_3$), 0.91 (s, 3H, $CH_3$), 0.86–1.07 (m, 2H), 1.11–1.38 (m, 4H), 1.22 (s, 9H, $^tBu$), 1.44–1.75 (m, 7H), 1.92–2.27 (m, 5H), 3.35 (dd, J=12.9, 3.3 Hz, 1H, H-5), 4.58 (dd, J=12.5, 4.5 Hz, 1H, H-2), 6.86 (s, 1H, NH), 8.93 (s, 1H, OH).

NMR-$^{13}$C (DMSO-d6): 12.2 ($CH_3$), 13.4 ($CH_3$), 20.7 ($CH_2$), 22.8 ($CH_2$), 22.9 ($CH_2$), 24.1 ($CH_2$), 28.7 ($CH_3$, $^tBu$), 30.0 ($CH_2$), 33.9 (CH), 37.2 ($CH_2$) 40.8 (C), 43.4 ($CH_2$), 44.3 (C), 49.9 (C), 50.9 (CH), 54.8 (CH), 55.4 (CH), 58.4 (CH), 61.7 (CH), 104.8 (C, $C_3$), 147.1 (C, $Cl_3C$), 151.3 (C, carbonyl), 158.6 (c, carbonyl), 171.0 (C, amide).

EXAMPLE 6

Compound of Formula (V), Wherein $R^1$ is t-butylamine and $R^5$ is Bromine 74.13 g of the 2-bromo-3-hydroxyoxazolidinedione obtained in Example 3 are dissolved in 1.483 mL of methanol. 21.2 g of ground potassium permanganate are added at room temperature, and the resulting mixture is stirred until the reaction is finished (10 minutes). 59.3 mL of water are added, and it is stirred for 45 minutes, then the mixture is filtered by means of a filter aid and washed, portionwise, with a mixture of 80 mL of methanol and 3.2 mL of water. The mixture is evaporated to dryness and dried. 73.0 g of crude 17β-(N-t-butylcarbomoyl)-2-bromo-4-aza-5α-androstan-3-one are obtained as mixture of isomers in the position 2.

The crude thus obtained is suspended in 300 mL of methanol, 400 mL of water are dropwise added and the resulting suspension is stirred for 1 hour at room temperature and at −5° C. for an additional hour. The reaction mixture is filtered and dried, obtaining 49.93 g of purified 17β-(N-t-butylcarbomoyl)-2-bromo-4-aza-5α-androstan-3-one.

NMR-$^1$H (CDCl$_3$) (More polar isomer): 0.68 (s, 3H, $CH_3$), 0.70–0.79 (m, 1H), 0.92–1.05 (m, 3H), 1.13 (s, 3H, $CH_3$), 1.21–1.28 (m, 3H), 1.35 (s, 9H, $^tBu$), 1.43–1.57 (m, 3H), 1.66–1.77 (m, 3H), 1.92–2.03 (m, 2H), 2.05–2.17 (m, 2H), 2.45 (d, J=13.6 Hz, 1H, $H_e$-1), 3.05 (dd, J=12.2, 3.6 Hz, 1H, H-5), 4.69 (dd, J=8.3, 1.8 Hz, 1H, H-2), 5.15 (s, 1H, H—N), 7.04 (s, 1H, H—N).

NMR-$^{13}$C (CDCl$_3$) (More polar isomer): 12.7 ($CH_3$), 13.0 ($CH_3$), 21.1 ($CH_2$), 23.0 ($CH_2$), 24.1 ($CH_2$), 26.3 ($CH_2$), 28.9 ($CH_3$, $^tBu$), 29.3 ($CH_2$), 34.3 (CH), 36.4 (C), 38.2 ($CH_2$), 41.7 (CH), 43.6 (C), 44.7 ($CH_2$), 50.9 (C), 51.3 (CH), 55.3 (CH), 57.3 (CH), 60.7 (CH), 168.4 (C, carbonylic), 171.5 (C, carbonylic).

EXAMPLE 7

Compound of Formula (V), Wherein $R^1$ is Methoxy and $R^5$ is Bromine 13.38 g of the 2-bromo-3-hydroxyoxazolidinedione obtained in Example 4 are suspended in 270 mL of methanol and cooled at −5° C. 4.15 g of ground potassium permanganate are added and stirred maintaining the temperature for 10 minutes. 250 mL of methylene chloride and 10 mL of water are added and the reaction mixture is stirred at room temperature for an additional 45 minutes. Then, it is filtered by means of a filter aid, and the solution is evaporated to dryness, obtaining 11.2 g of crude 17β-(methoxycarbonyl)-2-bromo-4-aza-5α-androstan-3-one which, once purified by flash chromatography, provides 3.26 g of 17β-(methoxycarbonyl)-2-bromo-4-aza-5α-androstan-3-one (sum of isomers).

NMR-$^1$H (CDCl$_3$) (Non-polar isomer): 0.63 (s, 3H, $CH_3$), 0.82–0.89 (m, 1H), 0.89 (s, 3H, $CH_3$), 0.93–1.12 (m, 2H), 1.18–1.45 (m, 5H), 1.51–1.85 (m, 5H), 1.88–2.00 (m, 2H), 2.05–2.15 (m, 1H), 2.33 (t, J=9.2 Hz, 1H), 2.56 (dd, J=13.6, 8 Hz, 1H), 3.20 (dd, J=12.4, 3.6, 1H, H-5), 3.64 (s, 3H, $OCH_3$), 4.49 (dd, J=10.8, 7.6, 1H, H-2), 6.80 (s, 1H, H—N).

NMR-$^{13}$C (CDCl$_3$) (Non-polar isomer): 11.52 ($CH_3$, Me), 13.52 ($CH_3$, Me), 20.93 ($CH_2$), 23.48 ($CH_2$), 24.26 ($CH_2$), 26.62 ($CH_2$), 29.29 ($CH_2$), 34.65 (CH), 37.90 ($CH_2(CH_2)$), 38.73 (C), 42.91 (CH), 44.06 (C), 46.56 ($CH_2$), 50.75 (CH), 51.26 ($CH_3$, $OCH_3$), 55.02 (CH), 55.12 (CH), 60.79 (CH), 167.90 (C, $C_3$), 174.25 (C, $C_{20}$).

EXAMPLE 8

Compound of Formula (V), Wherein $R^1$ is t-butylamine and $R^5$ is Trichloromethylsulfonyl 7.24 g of the 2-(trichloromethylsulfonyl)-3-hydroxyoxazolidinedione obtained in Example 5 are dissolved in 145 mL of methanol, 1.82 g of ground potassium permanganate are added, the mixture is stirred until the reaction is completed (5 minutes), 5.8 mL of water are added and it is stirred at room temperature for 1 hour. Then, it is filtered by means of a filter aid and the mother liquors are evaporated until reducing to 30 mL final volume. 35 ml of water are added dropwise, the suspension is cooled at 0° C. for 1.5 hours, filtered and dried, obtaining 4.60 g of 17β-(N-t-butylcarbomoyl)-2-(trichloromethylsulfonyl)-4-aza-5α-androstan-3-one as a white solid.

EXAMPLE 9

Compound of Formula (I), Wherein $R^1$ is t-butylamine 110.3 g of potassium tert-butoxide are dissolved under nitrogen in 350 mL of anhydrous dimethylformamide. The reaction mixture is cooled at −5° C. and a solution of 49.93 g of 17β-(N-t-butylcarbomoyl)-2-bromo-4-aza-5α-androstan-3-one (obtained in Example 6) in 150 mL of anhydrous dimethylformamide is slowly added, the temperature is controled such that it does not rise above 5° C. The −5° C. temperature is maintained for 15 minutes and 90 mL of glacial acetic acid are added dropwise, keeping the temperature below 8° C. The reaction mixture is slowly diluted with 2 L of brine, stirred for 1 hour and filtered. The wet isolated solid is resuspended in 1 L of water, stirred for 1 hour, filtered and dried, obtaining 43.37 g of crude finasteride.

38.49 g of crude finasteride thus obtained are suspended in 450 mL of n-butyl acetate and taken to reflux. The reaction mixture is heat filtered by means of a filter aid, removing the insolubles. The filter aid is washed with 150 mL of boiling n-butyl acetate, and the solution is distilled under vacuum conditions until reducing the volume to 150 mL. Then, 1.5 mL of water are added, the reaction mixture is left to reach room temperature, stirred for 2 hours, cooled at −5° C. and stirring is maintained for an additional hour. Then, the suspension is filtered and washed with 30 mL of cold n-butyl acetate and dried in a hot air circulation oven, obtaining 30.62 g of finasteride. The purification is repeated once more under the same conditions and ratios, obtaining 27.6 g of purified finasteride.

NMR-$^1$H (CDCl$_3$): 0.66 (s, 3H, CH$_3$), 0.93 (s, 3H, CH$_3$), 0.96–1.12 (m, 3H), 1.18–1.28 (m, 2H), 1.32 (s, 9H, $^t$Bu), 1.36–1.58 (m, 3H), 1.59–1.74 (m, 5H), 1.92–2.20 (m, 3H), 3.28 (dd, J=11.6, 4.6 Hz, 1H, H-5), 5.11 (s, 1H, H—N), 5.77 (dd, J=9.9, 2.2 Hz, 1H, H-2), 6.49 (s, 1H, H—N), 6.75 (d, J=10.0 Hz, 1H, H-1).

NMR-$^{13}$C (CDCl$_3$): 11.9 (CH$_3$), 13.2 (CH$_3$), 21.1 (CH$_2$), 23.1 (CH$_2$), 24.2 (CH$_2)$, 25.7 (CH$_2$), 28.9 (CH$_3$, $^t$Bu), 29.3 (CH$_2$), 35.2 (CH), 38.3 (CH$_3$), 39.2 (C), 43.8 (C), 47.5 (CH), 51.0 (C, $^t$Bu), 55.5 (CH), 57.3 (CH), 59.5 (CH), 122.9 (CH, C$_2$), 150.8 (CH, C$_1$), 166.7 (C, carbonylic), 171.5 (C, carbonylic).

EXAMPLE 10

Compound of Formula (I), Wherein $R^1$ is Methoxy 2.43 g of potassium tert-butoxide are dissolved under nitrogen in 7 mL of anhydrous dimethylformamide. The solution formed is cooled at −5° C., and a mixture of 1 g of 17β-(methoxycarbonyl)-2-bromo-4-aza-5α-androstan-3-one obtained in example 7 in 3 mL of anhydrous dimethylformamide are added slowly at such a rate that the temperature does not rise above 5° C. The −5° C. temperature is maintained for an additional 15 minutes, and then 2 mL of acetic acid are added dropwise, keeping the temperature below 8° C. The reaction mixture is diluted slowly with 40 mL of brine, stirred for 1 hour and filtered. The wet isolated solid is resuspended in 20 mL of water, stirred for 1 hour, filtered and dried, obtaining 0.68 g of crude 17β-(methoxycarbonyl)4-aza-5α-androst-1-ene-3-one.

NMR-$^1$H (CDCl$_3$): 0.65 (s, 3H, CH$_3$), 0.94 (s, 3H, CH$_3$), 0.97–1.16 (m, 3H), 1.20–1.32 (m), 1.33–1.42 (m), 1.55–1.82 (m), 2.00–2.13 (m), 2.31–2.36 (m), 3.29 (dd, J=12.0, 4.3 Hz, 1H, H-5), 3.65 (s, 3H, OCH$_3$), 5.77 (dd, J=9.9, 2.2 Hz, 1H, H-2), 6.40 (s, 1H, H—N), 6.77 (d, J=10.0 Hz, 1H, H-1).

NMR-$^{13}$C (CDCl$_3$): 12.9 (CH$_3$), 13.6 (CH$_3$), 21.1 (CH$_2$), 23.5 (CH$_2$), 24.3 (CH$_2$), 25.6 (CH$_2$), 29.4 (CH$_2$), 35.4 (CH), 38.0 (CH$_2$), 39.3 (C), 44.2 (C), 47.5 (CH), 51.3 (CH$_3$, OCH$_3$), 55.0 (CH), 55.3 (CH), 59.6 (CH), 122.9 (CH, C$_2$), 150.9(CH, C$_1$), 166.8 (C, carbonyl), 174.3 (C, carbonyl).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A process for obtaining 17β-(substituted)-3-oxo-Δ$^{1,2}$-4-azasteroid of formula (I)

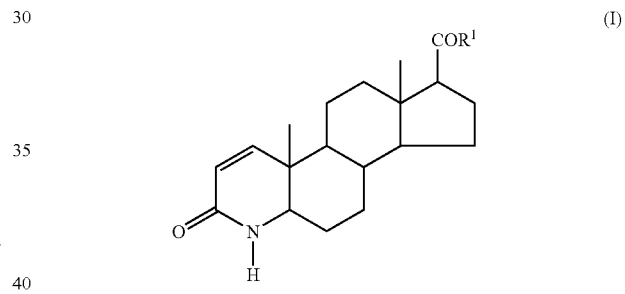

wherein
R1 can be a linear or branched alkyl group having 1 to 4 carbon atoms; OR2, wherein R2 is a linear or branched alkyl radical having 1 to 4 carbon atoms; or NR3R4, wherein R3 and R4, equal or different, represent hydrogen or a linear or branched alkyl radical having 1 to 4 carbon atoms, comprising the steps of:
a) cleaving the oxazolidinedione ring present in a 2-(substituted)-3-hydroxyoxazolidinedione of formula (IV):

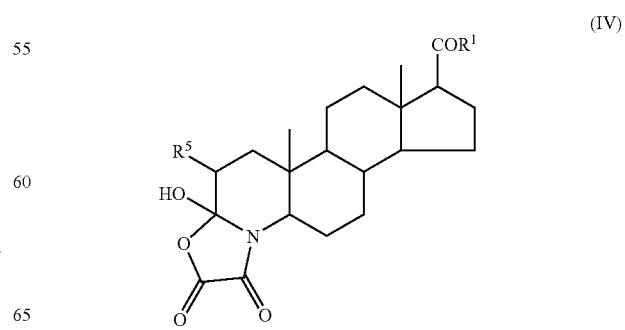

wherein R¹ has the same meaning as above and R⁵ is selected between Br and trichloromethylsulfonyl;

to obtain a 2-(substituted)-3-oxo-4-azasteroid of formula (V):

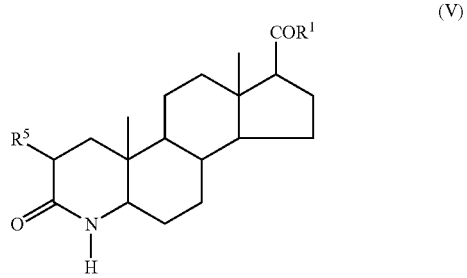

wherein R¹ and R⁵ have the same meaning as above; and b) removing the R⁵ substituent present in said compound of formula (V), together with a hydrogen at position 1, to produce said 17β-(substituted)-3-oxo-Δ$^{1,2}$-4-azasteroid of formula (I).

2. A process according to claim 1, wherein the cleavage of the oxazolidinedione ring present in the compound of formula (IV) is carried out by oxidation with potassium permanganate.

3. A process according to claim 2, wherein the cleavage of the oxazolidinedione ring present in the compound of formula (IV) is carried out by oxidation with potassium permanganate in an organic solvent chosen from among methanol, acetone, dichloromethane, 1,2-dichloroethane and mixtures thereof with water, at a temperature comprised between 0° C. and 80° C.

4. A process according to claim 1, wherein the removal of the R⁵ group in the compounds of general formula (V) is carried out with potassium t-butoxide in dimethylformamide.

5. A process according to claim 1, wherein the obtained compound of formula (I) is finasteride.

6. A compound of formula (IV)

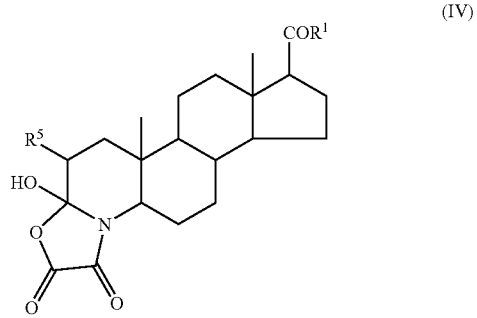

wherein
R¹ is a linear or branched alkyl group having 1 to 4 carbon atoms; OR², wherein R² is a linear or branched alkyl radical having 1 to 4 carbon atoms; or NR³R⁴, wherein R³ and R⁴, equal or different, represent hydrogen or a linear or branched alkyl radical having 1 to 4 carbon atoms, and R⁵ represents trichloromethanesulfonyl.

7. A compound according to claim 6 chosen from the compounds of formula (IV) wherein:

R¹ is t-butylamino and R⁵ is trichloromethanesulfonyl; and

R¹ is methoxy and R⁵ is trichloromethanesulfonyl.

8. A process for obtaining a compound of formula (IV) according to claim 6, comprising reacting a compound of formula (III)

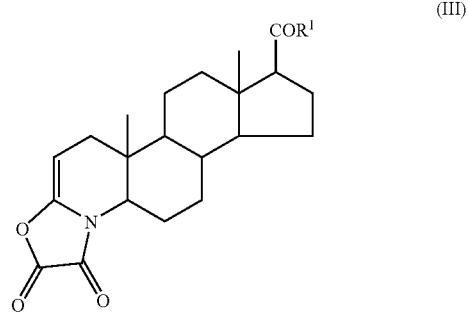

wherein
R² is a linear or branched alkyl group having 1 to 4 carbon atoms; OR², wherein R² is a linear or branched alkyl radical having 1 to 4 carbon atoms; qor NR³R⁴, wherein R³ and R⁴, equal or different, represent hydrogen or a linear or branched alkyl radical having 1 to 4 carbon atoms;

with a compound selected from between:
(i) a reagent capable of adding hypobromous acid to the double bond at position 2,3 of the compound of formula (III), the reagent comprising a compound selected from the group consisting of N-bromosuccinimide and 1,3-dibromo-5,5-dimethyihydantoin; and (ii) a trichioromethylsulfonyl halide, to produce said compound of formula (IV).

9. A process for obtaining a compound of formula (IV) according to claim 6, comprising:

a) reacting a 17β-(substituted)-3-oxo-4-azasteroid of formula (II):

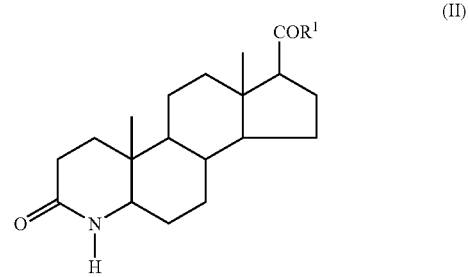

wherein
R¹ is a linear or branched alkyl group having 1 to 4 carbon atoms; OR², wherein R² is a linear or branched alkyl radical having 1 to 4 carbon atoms; or NR³R⁴, wherein R³ and R⁴, equal or different, represent hydrogen or a linear or branched alkyl radical having 1 to 4 carbon atoms;

with oxalyl chloride to produce a vinylidenyloxazolidinedione of formula (III):

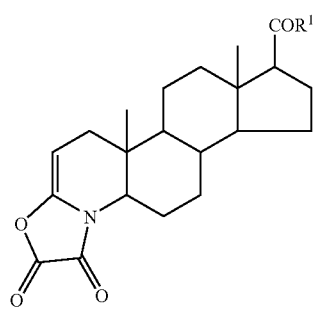

(III)

wherein R¹ has the same meaning as above; and b) reacting said compound of formula (III) with a compound selected between:

(i) a reagent capable of adding hypobromous acid to the double bond at position 2,3 of the compound of formula (III)), the reagent comprising a compound selected from the group consisting of N-bromosuccinimide and 1,3-dibromo-5,5-dimethylhydantoin; and;

(ii) a trichloromethylsulfonyl halide, to produce said compound of formula (IV).

10. A process according to claim 8, wherein said reagent capable of adding hypobromous acid to the double bond at position 2,3 is chosen from among N-bromosuccinimide, 1,3-dibromo-5,5-dimethylhydantoin and mixtures thereof, in an organic solvent, in presence of an acid, at a temperature comprised between −20° C. and 25° C.

11. A process according to claim 10, wherein said organic solvent is acetone and said acid is perchloric acid in aqueous solution.

12. A process according to claim 8, wherein the reaction of the compound of formula (III) with said trichloromethylsulfonyl halide is carried out in an organic solvent, in presence of a base, at a temperature comprised between −10° C. and 80° C.

13. A process according to claim 12, wherein said organic solvent is methylene chloride and said base is diisopropylethylamine.

14. A process for producing a 17β-(substituted)-3-oxo-Δ$^{1,2}$-4-azasteroid of formula (I)

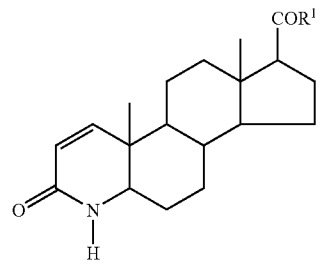

(I)

wherein
R¹ is a linear or branched alkyl group having 1 to 4 carbon atoms; OR², wherein R² is a linear or branched alkyl radical having 1 to 4 carbon atoms; or NR³R⁴, wherein R³ and R⁴, equal or different, represent hydrogen or a linear or branched alkyl radical having 1 to 4 carbon atoms, comprising the steps of:

a) reacting a 17β-(substituted)-3-oxo-4-azasteroid of formula (II):

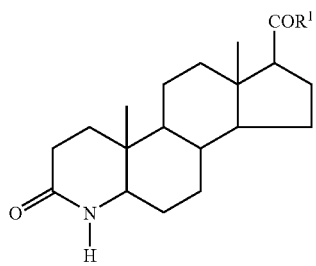

(II)

wherein
R¹ is a linear or branched alkyl group having 1 to 4 carbon atoms; OR², wherein R² is a linear or branched alkyl radical having 1 to 4 carbon atoms; or NR³R⁴, wherein R³ and R⁴, equal or different, represent hydrogen or a linear or branched alkyl radical having 1 to 4 carbon atoms, with oxalyl chloride to produce a vinylidenyloxazolidinedione of formula (III):

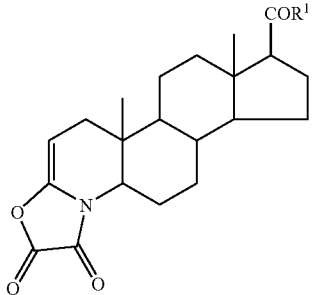

(III)

wherein R¹ has the same meaning as above;

b) reacting said compound of formula (III) with a compound selected between:

(i) a reagent capable of adding hypobromous acid to the double bond at position 2,3 of the compound of formula (III); and (ii) a trichloromethylsulfonyl halide, to produce said compound of formula (IV):

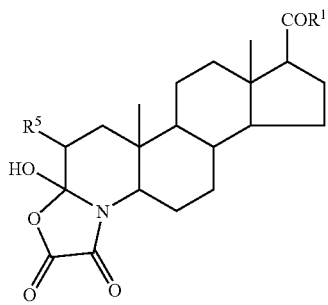 (IV)

wherein
  R[1] has the same meaning as above, and
  R[5] is selected between Br and trichloromethylsulfonyl,
c) cleaving the oxazolidinedione ring present in said compound of formula (IV) to produce a compound of formula (V):

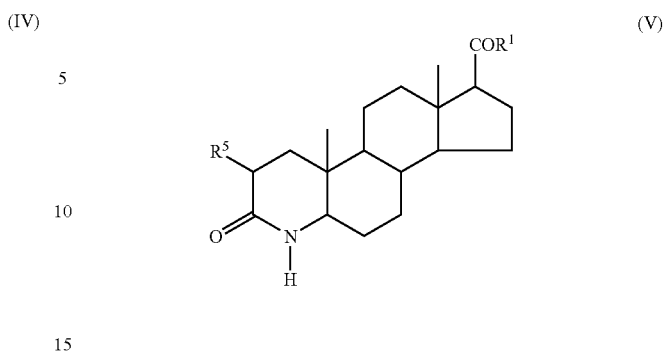

wherein R[1] and R[5] have the same meaning as above; and
d) removing the R5 substituent present in said compound of formula (V), together with a hydrogen at position 1, to produce said 17β-(substituted)-3-oxo-Δ1,2-4-azasteroid of formula (I).

15. A process according to claim 14, wherein the obtained compound of formula (I) is finasteride.

* * * * *